United States Patent [19]

Pettman et al.

[11] Patent Number: 4,798,845

[45] Date of Patent: Jan. 17, 1989

[54] IMIDAZOLE DERIVATIVES, THEIR PREPARATION AND THEIR USE AS FUNGICIDES

[75] Inventors: Roger B. Pettman, Wychling; Nicholas S. Wells, London, both of England

[73] Assignee: Shell Internationale Research Maatschappij, B.V., The Hague, Netherlands

[21] Appl. No.: 71,454

[22] Filed: Jul. 9, 1987

[30] Foreign Application Priority Data

Jul. 14, 1986 [GB] United Kingdom ................. 8617083

[51] Int. Cl.⁴ .................... C07D 233/66; A01N 43/50
[52] U.S. Cl. ..................................... 514/400; 548/343
[58] Field of Search ......................... 548/343; 514/400

[56] References Cited

U.S. PATENT DOCUMENTS 4,208,411  6/1980  Ikura et al. ........................... 548/341
4,391,804  7/1983  Ohyama et al. ...................... 548/341

OTHER PUBLICATIONS

Chemical Abstracts, vol. 104, No. 21, Abstract No. 186,415h, May 26, 1986.

Primary Examiner—Mary C. Lee
Assistant Examiner—Zinna Northington

[57] ABSTRACT

The invention provides imidazole derivatives of the general formula I:

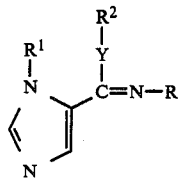

or a salt thereof, in which R represents an optionally substituted phenyl group, $R^1$ represents an optionally substituted alkyl, cycloalkyl, alkenyl, aryl or aralkyl group, $R^2$ represents an optionally substituted alkynyl group and Y represents an oxygen or sulphur atom; processes for their preparation and their use as fungicides.

9 Claims, No Drawings

IMIDAZOLE DERIVATIVES, THEIR PREPARATION AND THEIR USE AS FUNGICIDES

This invention relates to certain imidazole derivatives, to a process for their preparation and to the use of such derivatives as fungicides.

EP-A-91056 (BASF) discloses a class of 5-substituted-4-methylimidazole compounds of formula

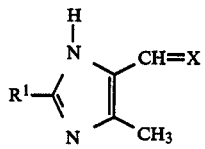

wherein X is inter alia

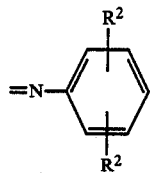

$R^1$ is hydrogen or an aliphatic moiety and each $R^2$ is independently hydrogen, an aliphatic moiety, a halogen atom or an alkoxy group. The compounds are disclosed as starting materials for plant protection compounds, dyestuffs and pharmaceuticals.

West German Offenlegungsschrift No. 3 217 094 (Hoechst) discloses the preparation of various imidazole-5-carboxylic acid derivatives of formula

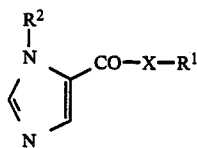

wherein $R^2$ is a phenyl or benzhydryl group optionally substituted by one or more substitutents selected from halogen, $C_{1-4}$ alkoxy and $C_{1-4}$ alkyl moieties, X is O, S or —$NR^1$— and $R^1$ is H, phenyl, $C_{2-6}$ alkenyl, optionally substituted $C_{1-12}$ alkyl or, when X is O or S, a metal cation or ammonium. These derivatives are described as having fungicidal, herbicidal and plant-growth regulant activity, and the compounds wherein $R^2$ is an optionally substituted 2,6-dialkylphenyl group are claimed to be novel.

There has now been discovered a novel class of 5-substituted imidazole derivatives which has been found to have useful fungicidal activity.

According to the present invention there is therefore provided a compound of the general formula I:

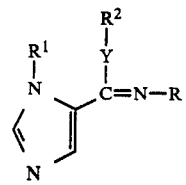

or a salt thereof, in which R represents an optionally substituted phenyl group, $R^1$ represents an optionally substituted alkyl, cycloalkyl, alkenyl, aryl or aralkyl group, $R^2$ represents an optionally substituted alkynyl group and Y represents an oxygen or sulphur atom.

The alky, alkenyl and alkynyl groups may be linear or branched and preferably contain from 1 to 8 carbon atoms.

Optional substituents include for example halogen atoms and alkyl, alkoxy, haloalkyl, haloalkoxy, hydroxy, cyano, nitro, amino, carboxy, alkoxycarbonyl, phenyl, phenoxy, phenylthio, alkylthio and alkylsulphonyl groups, any alkyl moiety present preferably having up to 4 carbon atoms.

Preferably, $R^2$ represents a group of the formula —$(CR^4R^5)_m$—C≡C—$R^6$ where m is 1 to 4 and $R^4$, $R^5$ and $R^6$ each independently represent a hydrogen atom or an optionally substituted alkyl or alkenyl group, provided that, when m is 1, $R^4$ is a hydrogen atom.

A preferred group of compounds of formula I are those having the formula II:

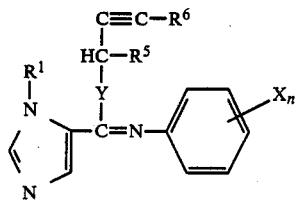

where $R^1$, $R^5$, $R^6$ and Y are as defined above, the or each X represents a halogen, preferably cholorine, atom, or a group selected from a trifluoromethyl group, a methoxy group and a nitro group and n is 1 or 2. Preferred compounds of formula II are those in which n is 2 and each X represents a chlorine atom, preferably substituted at the o- and p- positions. Other preferred compounds are those where n is 2, one X represents o-trifluoromethyl or o-nitro and the other X represents p-chloro and those where n is 1 and X represents p-methoxy.

$R^1$ preferably represents a lower alkyl group (suitably having from 1 to 8 carbon atoms).

$R^4$, $R^5$ and $R^6$ each preferably represent a hydrogen atom or a lower alkyl group (suitably having from 1 to 8 carbon atoms). More preferably, $R^4$, $R^5$ and $R^6$ each represent a hydrogen atom or a methyl group. Preferably m is 1 or 2 and $R^4$, $R^5$ and $R^6$ each represent hydrogen atoms. Y is preferably an oxygen atom.

A particularly preferred group of compounds are those compounds of formula I in which R represents a 2,4-dichlorophenyl, 2,5-dichlorophenyl, 4-chloro-2-trifluoromethylphenyl, 4-methoxyphenyl or a 4-chloro-2-nitrophenyl group, $R^1$ represents a $C_{1-4}$ alkyl group, Y represents an oxygen atom and $R^2$ is of the formula —$(CH_2)_m$—C≡C—H where m is 1 or 2.

The compounds of formula (I) may be prepared and used in the form of imidazole salts, for instance, salts with suitable inorganic moieties such as reactive metals or mineral acids, e.g. hydrochloric acid.

The present invention also provides a process for the preparation of a compound of formula I which comprises reacting a compound of formula III:

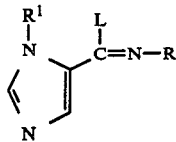

III where R and $R^1$ are as defined above and L is a leaving group, with a compound of formula IV:

$$H-Y-R^2 \quad \quad IV$$

where $R^2$ and Y are as defined above, in the presence of a base.

The leaving group L may conveniently be a halogen atom, preferably a chlorine atom.

In some cases, e.g. when Y is —O—, the compound of formula IV may advantageously be treated with the base prior to admixture with the compound of formula III. Thus, for example, when the compound of formula IV is an alkanol, the mixture of the compound of formula IV with base may be achieved by dissolving sodium metal in the alkanol or by reaction of the alkanol with sodium hydride. In cases where X is —S—, the base may conveniently be a base such as pyridine.

The above process may be effected in the absence of an additional inert solvent, for instance, when the compound of formula IV is in excess and the excess acts as solvent, or in cases when for instance, pyridine is used as the base and itself acts as a solvent. Alternatively, an additional inert solvent may be present. Suitable solvents include dimethoxyethane, dimethylsulphoxide, N,N-dimethylformamide and tetrahydrofuran.

Compounds of formula III where L is a halogen, may conveniently be prepared by reacting a compound of formula V:

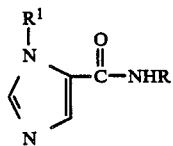

V where R and $R^1$ are as defined above, with a halogenating agent. Suitable halogenating agents include thionyl chloride, phosphorous pentachloride, phosphorous trichloride and phosphorous tribromide. Such reaction may, if desired, be effected in the presence of an inert solvent such as toluene, benzene, diethyl ether or tetrahydrofuran.

Compounds of formula V are either known compounds or can be prepared by processes analogous to known processes, e.g. processes described by R. G. Jones, J. Am. Chem. Soc. 71 (1949), 644, or DE-A-3 217 094 referred to above.

Further in accordance with the invention there is provided a fungicidal composition which comprises a carrier and, as active ingredient, at least one compound of formula I or a salt thereof as defined above.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; synthetic hydrated silicon oxides and synthetic calcium or aluminum silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier component which is a surface-active agent facilitates this process of dilution. Thus preferably at least one carrier component in a composition according to the invention is a surface-active agent. For example, the composition may contain at least two carrier components, at least one of which is at surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or proplylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecyl benzene sulphonate; and polymers of ethylene oxide and copolymers of ethylene oxide and propylene oxide.

The composition of the invention may for example be formulated as wettable powders, dusts, granules, solutions, emulsifiable concentrates, emulsions, suspension concentrates and aerosols. Wettable powders usually contain 25, 50 or 75% by weight of active ingredient and usually contain, in addition to solid inert carrier, 3–10% by weight of dispersing agent and, where necessary, 0–10% by weight of stabiliser and/or other additives such as penetrants or stickers. Dusts are usually formulated as a dust concentrate having a similar composition to that of a wettable powder but without a dispersant, and may be diluted in the field with further solid carrier to give a composition usually containing 0.5–10% by weight of active ingredient. Granules are usually prepared to have a size between 10 and 100 BS mesh (1.676–0.152 mm), and may be manufactured by agglomeration or impregnation techniques. Generally, granules will contain 0.5–25% by weight active ingredient and 0–10% by weight of additives such as stabilisers, slow release modifiers and binding agents. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% by weight of active ingredient, 0.5–15% by weight of dispersing agents, 0.1–10% by weight of suspending agents such as protective colloids and thixotropic agents, 0–10% by weight of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example other compounds possessing pesticidal, especially insecticidal, acaricidal, herbicidal or fungicidal, properties.

Of particular interest in enhancing the duration of the protectant activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or a salt thereof, and a method for combating fungus at a locus, which comprises treating the locus, which may, for example, be plants subject to or subjected to fungal attack, seeds of such plants or the medium in which such plants are growing or are to be grown, with such a compound.

The present invention is of wide applicability in the protection of crop plants against fungal attack. Typical crops which may be protected include vines, grain crops such as wheat and barley, rice, beans and apples. The duration of protection is normally dependent on the individual compound selected, and also a variety of external factors, such as climate, whose impact is normally mitigated by the use of a suitable formulation. Application rates may typically be in the range 0.1 to 10 kg active ingredient per hectare (kg/ha), preferably 0.1 to 1 kg/ha.

The invention is further illustrated by the following examples.

EXAMPLE 1

Preparation of but-3-ynyl-N-(2,4-dichlorophenyl)-1-ethylimidazole-5-carboximidate

[(I): R = 2,4-dichlorophenyl; $R^1 = C_2H_5$; Y = O; $R^2 = HC \equiv C \cdot CH_2CH_2$—]

(A) 1-Chloro-N-(2,4-dichlorophenyl)-1-ethylimidazole-5-carboximidate

N-(2,4-Dichlorophenyl)-1-ethylimidazole-5-carboxamide (1.4g, 0.00493 mol) was refluxed in thionyl chloride (35 ml) for 2 hours. The excess thionyl chloride was evaporated off under reduced pressure to leave 1-chloro-N-(2,4-dichlorophenyl)-1-ethylimidazole-5-carboximidate as a solid residue.

(B) But-3-ynyl-N-(2,4-dichlorophenyl)-1-ethylimidazole-5-carboximidate 3-butyn-1-ol (1.4g, 0.02 mol) was added dropwise to a stirred suspension of sodium hydride (0.6 g, 0.015 mol, 60% dispersion in oil) in dry dimethylformamide (15 ml) under nitrogen and the reaction mixture was stirred at ambient temperature for 1 hour after the addition. The 1-chloro-N-(2,4-dichlorophenyl)-1-ethylimidazole-5-carboximidate obtained in (A) suspended in dry dimethylformamide (20 ml) was then added to the reaction mixture which was stirred at ambient temperature for a further 3 hours and allowed to stand overnight. The dimethylformamide was then evaporated off under reduced pressure and the residue dissolved in ether and washed with water. The ether layer was dried (MgSO$_4$), the solvent evaporated under reduced pressure and the solid residue chromatographed on silica using 2% v/v methanol/ether as eluant to afford but-3-ynyl-N-(2,4-dichlorophenyl)-1-ethylimidazole-5-carboximidate as a pale yellow oil (0.35 g, 21%).

Analysis: $C_{16}H_{15}Cl_2N_3O$ requires: C, 57.1; H, 4.5; N, 12.5%; found: C, 57.4; H, 4.6; N, 12.4%.

EXAMPLES 2 TO 6

By processes similar to that described in Example 1, the following further compounds in accordance with the invention were prepared as detailed in Table I below. In this table, the compounds are identified by reference to formula I.

TABLE 1

| Example | R | $R^1$ | Y | $R^2$ | mp (°C.) | Analysis Found (Theoretical) | | |
|---|---|---|---|---|---|---|---|---|
| 2 | 2,5-dichlorophenyl | CH$_3$— | 0 | HC≡CCH$_2$— | oil | C, 54.6; (C 54.5; | H, 3.6; H, 3.6; | N, 13.5% N, 13.6%) |
| 3 | 4-chloro-2-trifluoromethylphenyl | CH$_3$— | 0 | HC≡CCH$_2$— | 100–103 | C, 52.2; (C, 52.7; | H, 3.3; H, 3.2; | N, 12.3% N, 12.3%) |

TABLE 1-continued

| Example | R | R¹ | Y | R² | mp (°C.) | Analysis Found (Theoretical) | | |
| --- | --- | --- | --- | --- | --- | --- | --- | --- |
| 4 | 4-methoxyphenyl | CH₃— | 0 | HC≡CCH₂— | oil | C, 66.3; (C, 66.9; | H, 5.8; H, 5.6; | N, 15.2% N, 15.6%) |
| 5 | 4-chloro-2-nitrophenyl | CH₃— | 0 | HC≡CCH₂— | 160–162 | C, 52.8; (C, 52.75; | H, 3.6; H, 3.45; | N, 17.0% N, 17.6%) |
| 6 | 2,4-dichlorophenyl | CH₃CH₂— | 0 | HC≡CCH₂— | 69–70 | C, 55.5; (C, 55.9; | H, 4.0; H, 4.0; | N, 12.8% N, 13.0%) |

EXAMPLE 7

Fungicidal Activity

The fungicidal activity of the compounds of the invention was investigated by means of the following tests.

(a) Direct protectant activity against vine downy mildew (*Plasmopara viticola*; Pvp)

The test is a direct protectant one, using a foliar spray. The lower surfaces of leaves of whole vine plants (cv) Cabernet Sauvignon) are sprayed with a solution of active material in 1:1 v/v water/acetone containing 0.04%w "Triton X-155" (trade mark) (octylphenol polyoxyethylene surfactant), at a dosage of 1 kilogram of active material per hectare using a track sprayer which delivers 620 l/ha, and after a subsequent 24 hours under normal glasshouse conditions the lower surfaces of the leaves are inoculated by spraying with an aqueous solution containing 10⁴ zoosproangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct protectant activity against vine grey mould (*Botrytis cinerea*; Bcp)

The test is a direct protectant one using a foliar spray and is effected as described under (a), with the difference that the leaves are inoculated by spraying with an aqueous solution containing 10⁵ conidia/ml.

(c) Activity against wheat leafspot (*Leptosphaeria nodorum*; Ln.)

The test is a direct antisporulant one, using a foliar spray. Leaves of wheat plants (cv Mardler), at the single leaf stage, are inoculated by spraying with an aqueous suspension containing 8×10⁵ spores/ml. The inoculated plants are kept for 24 hours in a high humidity compartment prior to treatment. The plants are sprayed at a dosage of 1 kg. of active material per hectare using a track sprayer as described under (a). After drying, the plants are kept for 5 days under normal glasshouse conditions, followed by assessment. Assessment is based on the percentage of leaf area covered by sporulation compared with that on leaves of control plants.

(d) Activity against barley powdery mildew (*Erysiphe graminis* f.sp. hordei; Eg)

The test is a direct antisporulant one, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at a dosage of 1 kg. of active material per hectare using a track sprayer as described under (a). After drying, plants are returned to a compartment at ambient temperature and humidity for up to 7 days, followed by assessment. Assessment is based on the percentage of leaf area covered by sporulation compared with that on leaves of control plants.

(e) Activity against wheat brown rust (*Puccinia recondita*; Pr)

The test is a direct protectant one using a foliar spray. Wheat seedlings (cv Brigand) are grown to the 1–1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20" - Trade Mark). 18–24 hours after treatment, the seedlings are inoculated by spraying the plants from all sides with an aquous spore suspension containing about 10⁵ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C. The disease is assessed 10 days after inoculation on the basis of the percentage of the plant covered by sporulating pustules compared with that on the control plants.

(f) Activity against broad bean rust (*Uromyces fabae*; Uf)

The test is a direct antisporulant one using a foliar spray. Pots containing 1 plant per pot were inoculated by spraying an aqueous suspension, containing 5×10⁴ spores/ml plus a little "Triton X-155", onto the upper surface of each leaf 20–24 hours before treatment with test compound. The inoculated plants were kept overnight in a high humidity compartment, dried at glasshouse ambient temperature and then sprayed, on the left upper surface, at a dosage of 1 kg/ha of active material using a track sprayer as described under (a). After treatment the plants were kept at glasshouse temperature and assessment made 11–14 days after treatment. Symptoms are assessed on the relative density of sporulating pustules per plant compared with that on control plants.

(g) Activity against rice leaf blast (*Pyricularia oryzae*; Po)

The test is a direct eradicant one using a foliar spray. The leaves of rice seedlings (about 30 seedlings per pot) are sprayed with an aqueous suspension containing 10⁵ spores/ml 20–24 hours prior to treatment with the test compound. The inoculated plants are kept overnight in high humidity and then allowed to dry before spraying at a dosage of 1 kg of active material per hectare using a track sprayer as described under (a). After treatment the plants are kept in a rice compartment at 25°–30° C. and high humidity. Assessments are made 4–5 days after treatment and are based on the density of necrotic lesions and the degree of withering when compared with control plants.

(h) Activity against tomato early blight (*Alternaria solani*; As)

This test measures the contact prophylactic activity of test compounds applied as a foliar spray. Tomato seedlings (cv Outdoor Girl) are grown to the stage at which the second true leaf is expanded. The plants are treated using a track sprayer as described under (a). Test compounds are applied as solutions in a mixture of acetone and water (50:50 v/v) containing 0.4% surfactant ("TWEEN 20" - Trade mark).

One day after treatment the seedlings are inoculated by spraying the leaf upper surfaces with a suspension of *A. solani* conidia containing $10^4$ spores/ml. For 3 days after inoculation plants are kept moist in a glasshouse compartment at or near 100% RH and 21° C. Thereafter plants are kept under humid, but not saturated, conditions.

Disease is assessed 7 days after inoculation, based on the density and spread of lesions.

(i) Activity against wheat eyespot in-vitro (*Pseudocercosporella herpotrichoides*; PhI)

The test measures the in vitro activity of compounds against the fungus causing wheat eyespot.

The test compound is dissolved or suspended in acetone and is added to molten half strength Potato Dextrose Agar to give a final concentration of 100 ppm compound and 3.5% acetone. After the agar has set, plates are inoculated with 6 mm diameter plugs of agar/mycelium taken from a 14 day old culture of *P. herpotrichoides*.

Plates are incubated at 20° C. for 12 days and radial growth from the inoculation plug is measured.

(j) Activity against Fusarium in-vitro (*Fusarium species*; FsI)

This test measures the in vitro activity of compounds against a species of Fusarium that causes stem and root rots.

The test compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp.

Plates are incubated at 20° C. for 5 days and radial growth from the plug is measured.

The extent of disease control in all the above tests is expressed as a rating compared with either an untreated control or a diluent-sprayed-control, according to the criteria:
0 = less than 50% disease control
1 = about 50-80% disease control
2 = greater than 80% disease control
The results of the above tests are given in Table II below.

TABLE II

| Compound Example | Fungicidal Activity | | | | | | | | | |
|---|---|---|---|---|---|---|---|---|---|---|
| | Pvp | Bcp | Ln | Eg | Pr | Uf | Po | As | PhI | FsI |
| 1 | 1 | | 1 | 2 | | 1 | | 1 | | 2 |
| 2 | | | 2 | 2 | 2 | 1 | 2 | 1 | 2 | 2 |

TABLE II-continued

| Compound Example | Fungicidal Activity | | | | | | | | | |
|---|---|---|---|---|---|---|---|---|---|---|
| | Pvp | Bcp | Ln | Eg | Pr | Uf | Po | As | PhI | FsI |
| 3 | | | 2 | 2 | | 1 | | 1 | | 1 |
| 4 | | | 1 | 2 | | | | | | |
| 5 | 1 | | 1 | 2 | 1 | | | | 1 | 1 |
| 6 | | 1 | 2 | 2 | 2 | | 1 | 1 | 2 | 2 |

We claim:
1. A compound of formula

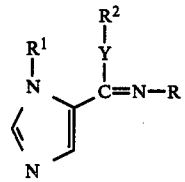

or a salt thereof, in which R represents a group of formula

where X is a substituent selected from the group consisting of halogen atoms, trifluoromethyl, methoxy and nitro groups and n is 1 or 2; $R^1$ represents a $C_{1-8}$ alkyl group; $R^2$ represents a group of formula $-(CR^4R^5)_m-C\equiv C-R^6$ where m is 1 to 4 and each of $R^4$, $R^5$ and $R^6$ represent a hydrogen atom or a $C_{1-8}$ alkyl group, provided that, when m is 1, $R^4$ is a hydrogen atom; and Y represents an oxygen or sulphur atom.

2. A compound according to claim 1 in which n is 2 and each X represents a chlorine atom.

3. A compound according to claim 1 or claim 2 in which Y represents an oxygen atom.

4. A compound according to claim 1 in which m is 1 or 2 and $R^4$, $R^5$ and $R^6$ each represent hydrogen atoms.

5. A fungicidal composition for protecting plants against fungal attack which comprises a carrier and, as active ingredient, a fungicidally effective amount of at least one compound of formula I or a salt thereof as defined in claim 1.

6. A fungicidal composition according to claim 5 which comprises two carriers, at least one of which is a surface active agent.

7. A method of combating fungus at a locus, which comprises treating the locus with a compound of formula I or a salt thereof as defined in claim 1.

8. A method according to claim 7 in which the locus comprises plants subject or subjected to fungal attack, seeds of such plants or the medium in which the plants are growing or are to be grown.

9. A compound according to claim 1 in which R represents a 2,4-dichlorophenyl, 2,5-dichlorophenyl, 4-chloro-2-trifluoromethylphenyl, 4-methoxyphenyl or 4-chloro-2-nitrophenyl group, $R^1$ represents a $C_{1-4}$ alkyl group, $R^2$ represents a group $-(CH_2)_m-C\equiv CH$ where m is 1 or 2 and Y represents an oxygen atom.

* * * * *